(12) United States Patent
Khuri-Yakub et al.

(10) Patent No.: US 11,305,133 B2
(45) Date of Patent: Apr. 19, 2022

(54) EFFICIENT ACOUSTIC ENERGY TRANSFER THROUGH SKULL VIA EXCITATION OF LAMB WAVES

(71) Applicant: The Board of Trustees of the Leland Stanford Junior University, Palo Alto, CA (US)

(72) Inventors: Butrus T. Khuri-Yakub, Palo Alto, CA (US); Kamyar Firouzi, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1053 days.

(21) Appl. No.: 15/937,549

(22) Filed: Mar. 27, 2018

(65) Prior Publication Data

US 2018/0280735 A1    Oct. 4, 2018

Related U.S. Application Data

(60) Provisional application No. 62/479,819, filed on Mar. 31, 2017.

(51) Int. Cl.
| | |
|---|---|
| *A61N 7/02* | (2006.01) |
| *A61N 7/00* | (2006.01) |
| *A61B 8/00* | (2006.01) |
| *A61B 18/00* | (2006.01) |
| *A61B 8/08* | (2006.01) |

(52) U.S. Cl.
CPC .............. *A61N 7/02* (2013.01); *A61N 7/00* (2013.01); *A61B 8/0808* (2013.01); *A61B 8/4483* (2013.01); *A61B 2018/00446* (2013.01); *A61N 2007/0021* (2013.01); *A61N 2007/0026* (2013.01); *A61N 2007/0056* (2013.01); *A61N 2007/0078* (2013.01); *A61N 2007/0082* (2013.01); *A61N 2007/0095* (2013.01); *G01N 2800/52* (2013.01)

(58) Field of Classification Search
CPC .... A61N 7/02; A61N 7/00; A61N 2007/0082; A61N 2007/0026; A61N 2007/0095; A61N 2007/0056; A61N 2007/0021; A61N 2007/0078; A61B 8/0808; A61B 8/4483; A61B 2018/00446; G01N 2800/52
See application file for complete search history.

(56) References Cited

U.S. PATENT DOCUMENTS

| | | | |
|---|---|---|---|
| 5,965,818 A | * | 10/1999 | Wang ............... G01B 17/02 73/598 |
| 6,420,816 B2 | | 7/2002 | Getman et al. |
| 7,175,599 B2 | | 2/2007 | Hynynen et al. |
| 8,617,073 B2 | | 12/2013 | Prus et al. |
| 8,852,104 B2 | | 10/2014 | Oralkan et al. |
| 2009/0198137 A1 | * | 8/2009 | Ragauskas ......... A61B 8/4227 600/449 |

(Continued)

*Primary Examiner* — Hien N Nguyen
(74) *Attorney, Agent, or Firm* — Lumen Patent Firm (57) ABSTRACT

We provide a novel technique for coupling focused ultrasound into the brain. The ultrasound beam can be used for therapy or neuro-modulation. We excite a selected Lamb wave mode in the skull that mode converts into longitudinal waves in the brain. The benefits of our approach is in improved efficiency, reduction in heating of the skull, and the ability to address regions in the brain that are close or far from the skull.

7 Claims, 11 Drawing Sheets

(56) References Cited

U.S. PATENT DOCUMENTS

2010/0268152 A1\* 10/2010 Oralkan ............... A61B 8/4281
604/22
2014/0243666 A1\* 8/2014 Moilanen ............. A61B 5/0097
600/437

\* cited by examiner

EFFICIENT ACOUSTIC ENERGY TRANSFER THROUGH SKULL VIA EXCITATION OF LAMB WAVES

CROSS REFERENCE TO RELATED APPLICATIONS

This application claims the benefit of U.S. provisional patent application 62/479,819, filed on Mar. 31, 2017, and hereby incorporated by reference in its entirety.

GOVERNMENT SPONSORSHIP

This invention was made with Government support under contract EB019005 awarded by The National Institutes of Health. The Government has certain rights in the invention.

FIELD OF THE INVENTION

This invention relates to providing acoustic energy to the brain of a patient though the skull of the patient.

BACKGROUND

Focused ultrasound energy is being utilized for both therapeutic and neuro-modulation applications. Brain metastases, the most common malignant brain tumors, occur in up to 40% of patients with cancer. Left untreated, prognosis is abysmal, with a life expectancy of 1 month. Surgery and radiation are typically combined to treat brain metastases. In order to minimize or avoid the risks of invasive surgery, such as bleeding and infection, and the toxic effects of radiation to the brain, such as decline in learning and memory, alternatives are being sought. One possible alternative, magnetic resonance guided focused ultrasound, is being researched as a noninvasive means of ablating brain tumors and of increasing delivery of cancer therapeutics through the blood-brain barrier.

Non-invasive neuro-modulation is central to treating diseases like stroke, multiple sclerosis, neuropathic pain, migraine, depression, etc. Transcranial Magnetic Stimulation (TMS) is currently the most common modality, however, with poor spatial selectivity and penetration depth. Ultrasound neuro-modulation is an emerging competing technique with superior spatial selectivity and penetration depth, and potentially a wider spectrum of applications.

Current techniques to transmit ultrasound into the brain have traditionally been implemented by means of a large-aperture spherical transducer having a very large number of single element transducers transmitting ultrasound beams through the skull. The geometric focus of these transducers limits the treatment envelope to the center of the brain, whereas the majority of cancers, especially metastases, occur along the periphery of the brain. In addition, because these transducers create waves that impinge perpendicularly on the skull and since the skull significantly attenuates ultrasound, the transmission coefficient is less than 30%. Furthermore, the major portion of the wave energy is trapped inside the skull and sets up standing waves, which effectively turns the skull into a resonator, and thus leads to excess heating and burn inside the skull. This consequently results in a requirement for active cooling to prevent burning of the bone or skin.

SUMMARY

We provide a novel transducer design capable of introducing ultrasound wave energy into the brain by selectively exciting leaky guided Lamb waves in the skull. The scientific premise of our approach relies on the development of a novel technology for introducing focused ultrasound waves into the brain. The proposed technology is a transducer that utilizes guided. Lamb waves in the skull as an efficient way of transmitting the ultrasound beam into the brain without significant attenuation. In a preferred Embodiment, the main constituents of the transducer array are wedge transducer elements arranged over a wedge ring to provide a focusing mechanism.

Such approach has not been attempted to handle transcranial ultrasound delivery, especially in treating regions of the brain that are away from the center of the brain which are presently not accessible using traditional ultrasound delivery. The existing technologies are limited to operate at frequencies below 1 MHz, and also need to provide cooling to avoid burning of the skull and tissue especially in high intensity focused ultrasound (HIFU) applications. The existing approach aims the skull at a normal incident angle, at which power transmission is inefficient. It cannot be operated to access different areas of the brain and is limited to deep brain treatments. The benefits of our approach is in improved efficiency, reduction in heating of the skull, the ability to address regions in the brain that are close or far from the skull, and the ability to operate at a more diverse range of frequencies. These features altogether provide a higher focusing gain for the same amount of input power, compared to the conventional approach. Furthermore, because of these unique features, our method can also be utilized in other transcranial applications such as neuro-modulation and treating bone cancers.

DETAILED DESCRIPTION

A) General Principles

A1) Overview

Figure 1:
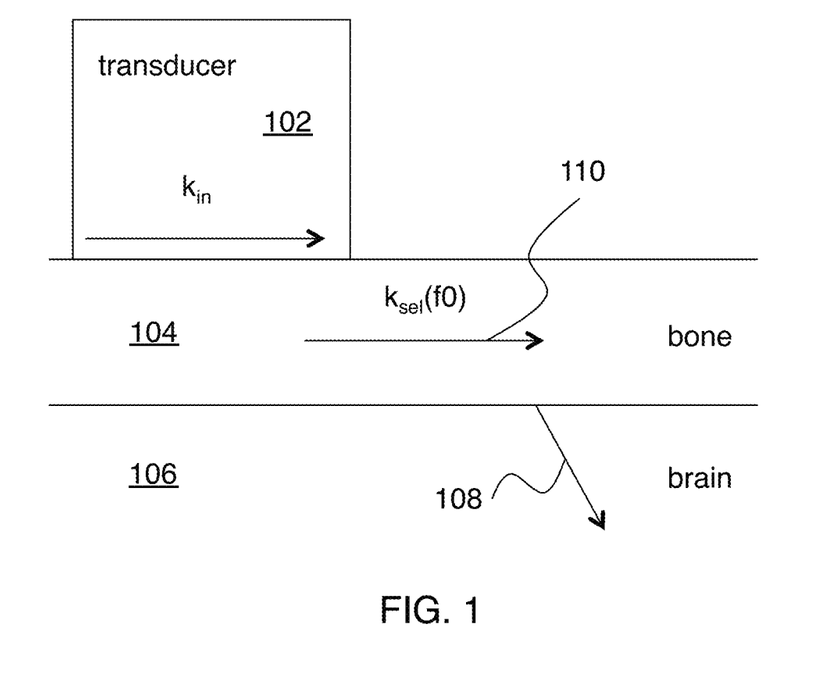
FIG. 1 is a phase matching diagram relating to embodiments of the invention.

FIG. 1 is a phase matching diagram relating to embodiments of the invention. An embodiment is an apparatus for providing acoustic energy to the brain of a patient where the apparatus includes acoustic transducer 102 configured to excite a selected Lamb wave mode 110, having propagation constant $k_{sel}(f0)$, in a skull 104 of the patient via phase matching to the selected Lamb wave mode. The selected Lamb wave mode 110 excites a longitudinal acoustic wave 108 in the brain 106. As indicated in more detail below, in preferred embodiments the acoustic transducer is configured as a ring to provide focusing of the longitudinal acoustic wave in the brain.

For time-harmonic waves (i.e., $\exp(-i2\pi ft)$ time dependence) propagating in a direction z, the main z-dependence of the wave amplitude is according to $\exp(ikz)$, where k is the propagation constant and i is $\mathrm{sqrt}(-1)$. For dispersive waves such as Lamb waves, k is a function of frequency f, which can be shown explicitly as k(f). To distinguish the various Lamb wave modes, the corresponding propagation constants can be indexed, which can be shown explicitly as $k_i(f)$, where i is the mode index.

In order to efficiently excite a selected Lamb wave mode (sel) at an operating frequency f0, the excitation should be concentrated at an input spatial frequency ($k_{in}$) that is the same as the spatial frequency of the selected Lamb wave mode ($k_{sel}(f0)$). In other words, we want $k_{in}=k_{sel}(f0)$. This condition is referred to as phase matching, and can be achieved in various ways. Phase matching need not be achieved exactly in order to provide sufficient benefits in practice. Equality of the relevant propagation constants to within +/−10% will suffice.

A2) Lamb Waves

A2.1) Lamb Waves (Guided Waves) in Bone/Skull

Figure 2A:
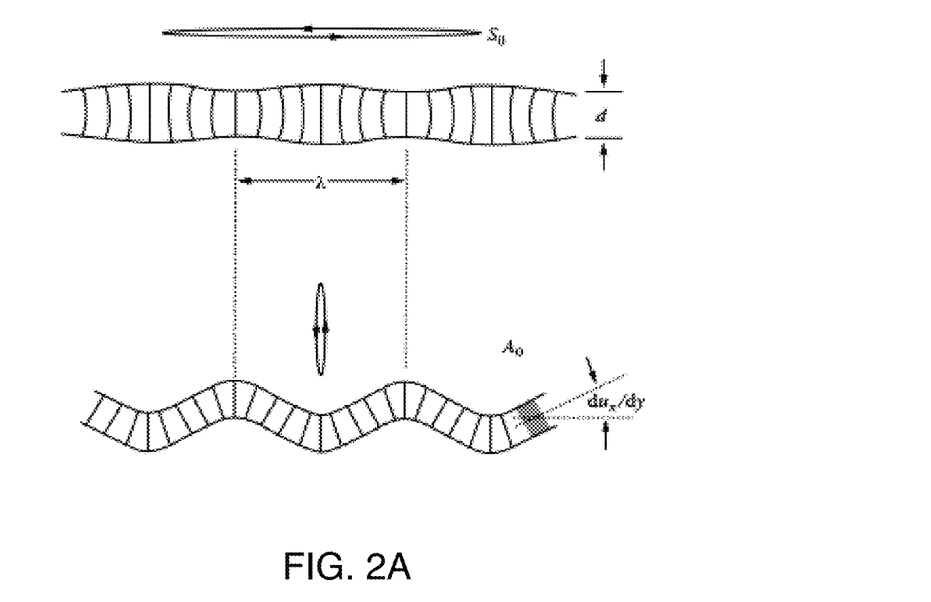
FIG. 2A shows exemplary deformation patterns for the S0 Lamb mode (top) and the A0 Lamb mode (bottom).
Figure 2B:
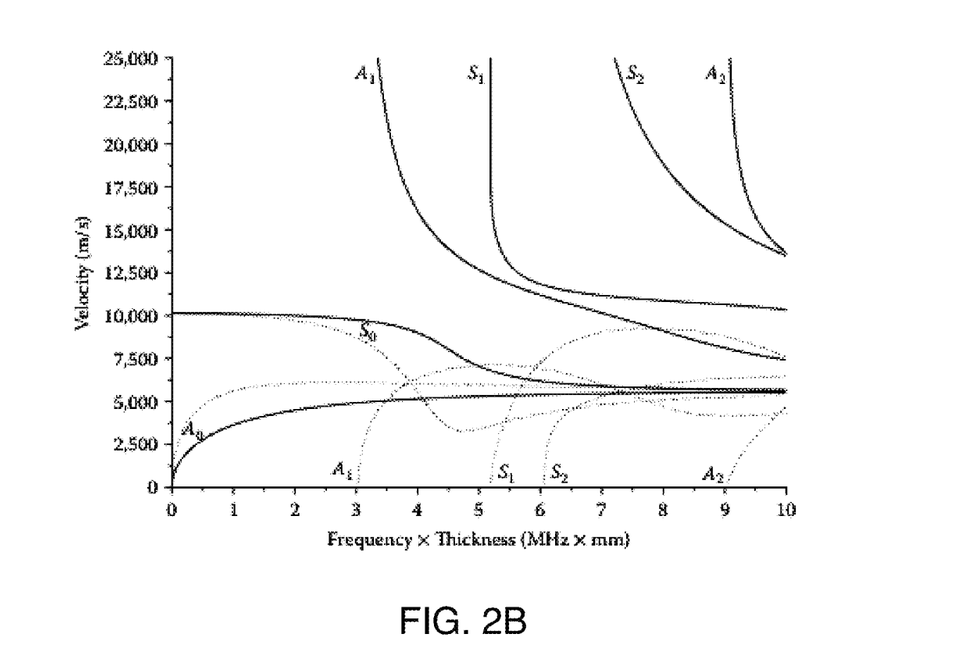
FIG. 2B show dispersion curves for several Lamb modes.

The human skull bone is transversely thin, and thus effectively, appears as an elastic waveguide that can support propagation of Lamb waves. Lamb waves are guided elastic waves that can propagate along bounded elastic media such as the skull bone. They can propagate without significant attenuation and can leak into the surrounding medium efficiently. The feasibility of exciting and propagating Lamb waves in bone has been studied and demonstrated previously in the literature. Lamb waves come in different frequency dependent modes. The dispersion curves and some of the mode-shapes are shown in FIGS. 2A-B. Dispersion is the dependence of the propagation velocity on the frequency. Dispersion is considered very weak in soft tissues and generally neglected. However, it has a strong effect on the propagation of Lamb waves. As it can be seen by the examples of the mode-shapes in FIG. 2A, Lamb waves couple the displacement of the upper and lower surfaces (outer and inner surfaces in the case of the skull), unlike the surface waves or bulk waves. Consequently, one can efficiently transmit energy from one side (outside the skull) to the other side (inside the skull). Lamb waves put adjacent to an acoustic medium (such as water or soft tissue) can leak acoustic energy into the acoustic medium by exciting acoustic waves in that acoustic medium. The leak rate is typically approximately a few wavelengths.

Acoustic attenuation in skull has a long-standing history of literature and research. Attenuation in skull is mainly due to two factors: (1) absorption of ultrasound energy, and (2) multiple scattering inside the skull due to its sub-wavelength heterogeneous structure. Propagation and attenuation of Lamb waves have been studied in the literature, according to which Lamb waves exhibit in general about 50% less attenuation than the normal-incident transmission approach, at around 1 MHz frequency).

Lamb waves (modes) can be selectively excited using a suitable wedge transducer design. Wedge transducers are efficient transducers that have conventionally been used in Surface Acoustic Wave (SAW) devices or for efficient excitation of Lamb waves. They provide a suitable mechanism for selectively exciting Lamb waves. The scientific merit of the wedge technique relies on the efficiency of the double-mode-conversion mechanism from longitudinal mode inside the wedge to the Lamb mode and from the Lamb mode to the longitudinal mode in the brain. Mode conversion efficiency of a wedge transducer has been the subject of extensive research for diverse applications of both surface and Lamb waves since the early days of ultrasonic guided wave technologies. Since skull bone exhibits significant impedance mismatch to tissue, the transmission at around the megahertz regime is inefficient (less than 30%). On the other hand, mode-conversion provides over 80% coupling efficiency one-way. Therefore, a double-mode-conversion process improves the transmission by over 35%, corresponding to 4-5 dB improvement.

A3) Transducer Approaches

Although the preceding description of Lamb waves focuses on using a wedge transducer for selectively exciting a Lamb wave mode, practice of the invention does not depend critically on the approach for generating the phase matched acoustic excitation. FIGS. 3A-D show several exemplary transducer approaches for providing an acoustic input that is phase matched to a Lamb mode.

Lamb waves inside a waveguide such as skull can be selectively excited using a suitable transducer design. Among the feasible techniques are wedge transducers (FIG. 3A), interdigital transducers/comb transducers (FIG. 3B), thermoacoustics (FIG. 3C), photoacoustics (aka optoacoustics) and X-ray acoustics (both on FIG. 3D). In the case of wedge and interdigital transducer designs, Lamb waves are excited through electromechanical transduction. The electromechanical transduction is provided by transducer elements that can be of a variety of types such as Piezoelectric, CMUT (capacitive micromachined ultrasonic transducers), PMUT (piezoelectric micromachined ultrasonic transducers), etc. The output mechanical energy is then coupled into the waveguide through an intermediate waveguide or direct contact. The width, angle, and material of the intermediate waveguide (in the wedge case) and the width of and spacing between the contact regions (in the interdigital case) determine the bandwidth and efficiency of these techniques. In the techniques of FIGS. 3C and 3D, the transduction mechanism is different and relies on the conversion of electromagnetic wave energy into ultrasound wave energy or a reversible thermoelectric/thermoelastic effect.

Figure 3A:
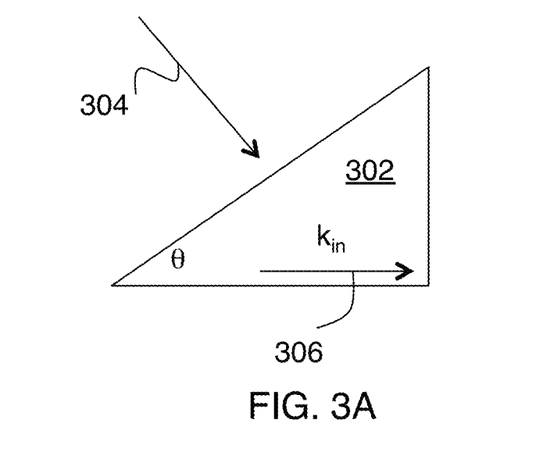
FIGS. 3A-D show several exemplary transducer approaches for providing an acoustic input that is phase matched to a Lamb mode.

FIG. 3A shows a wedge transducer 302 having a wedge angle θ that is driven by incident acoustic radiation 304 on the wedge face. For example a mechanical transducer can be mounted on the face of the wedge. For a wedge transducer with normal incidence on the face of the wedge, we have $k_{in}=f0*\sin(\theta)/c0$ for the acoustic input 306, where c0 is the longitudinal speed of sound in the wedge. Thus choice of the wedge angle of the electro-mechanical wedge transducer can provide the phase matching to the selected Lamb wave mode.

Figure 3B:
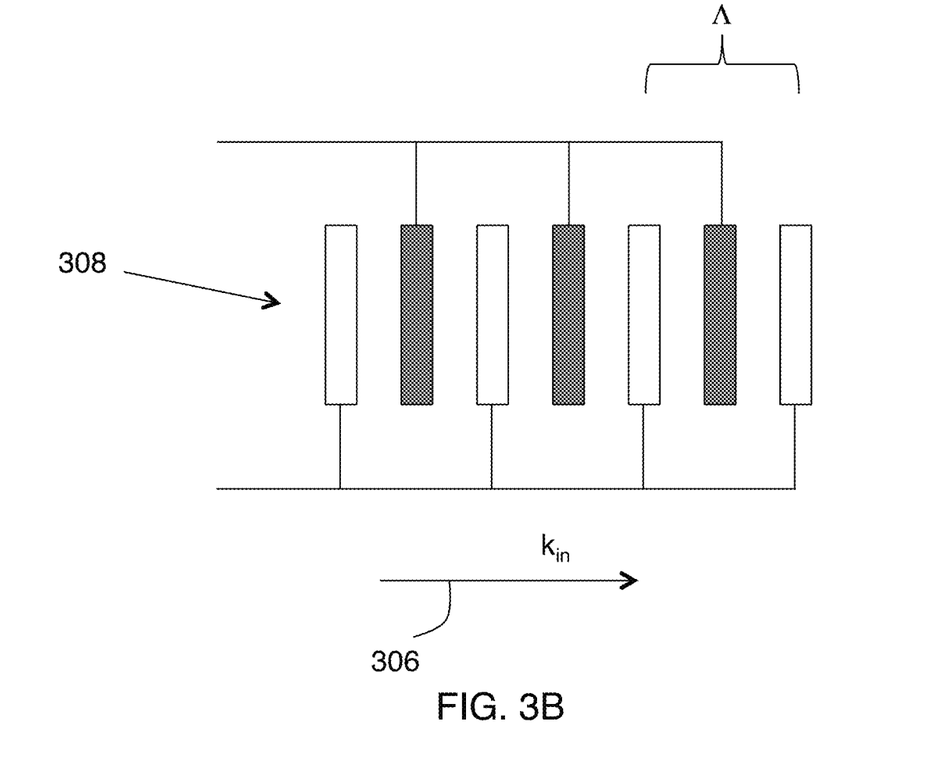
Figure 3C:
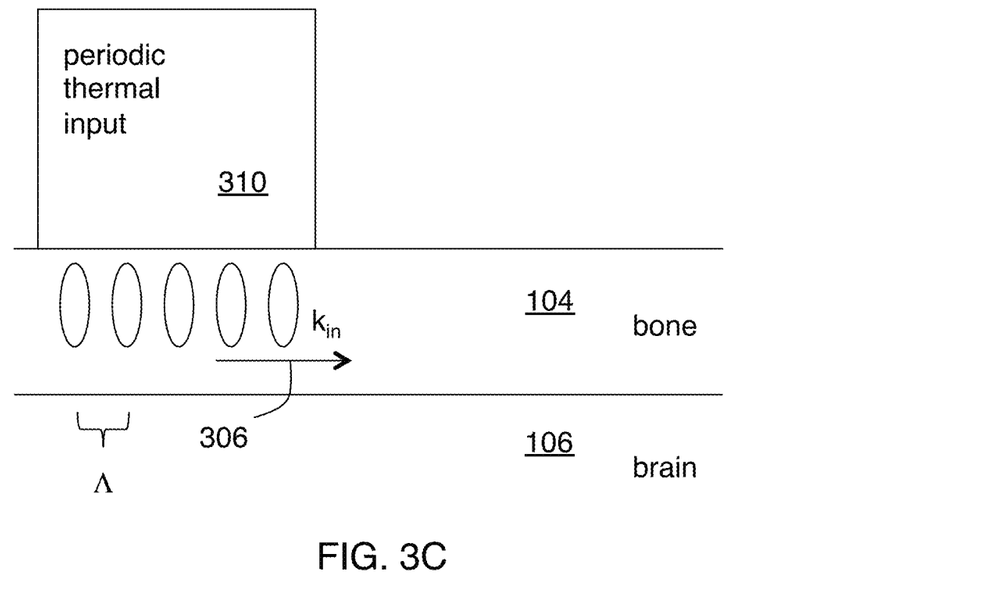
Figure 3D:
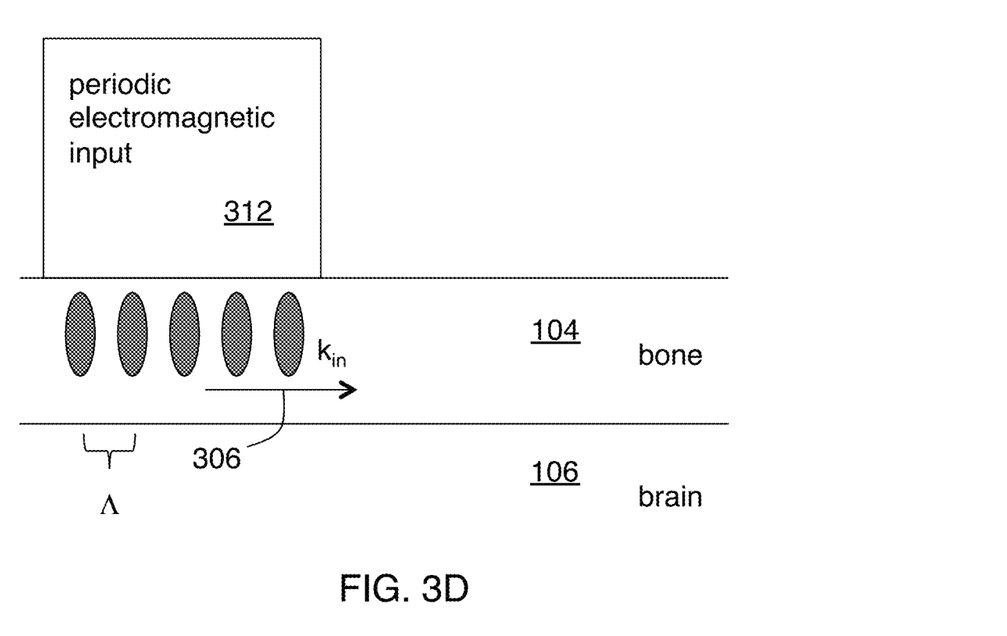

FIG. 3B shows an interdigitated transducer 308 having a periodicity of Λ. We have $k_{in}=2\pi/\Lambda$ for the acoustic input 306, where Λ is the period of the stimulus. Here this periodicity is defined by the spacing of the elements of the interdigitated transducer, as shown. Thus a periodicity of the electro-mechanical interdigitated transducer can provide the phase matching to the selected Lamb wave mode.

In thermoelectric effect shown on FIG. 3C, a reversible thermoelectric material 310 such as a Peltier material is brought in direct contact with the surface of the skull. The input electrical energy creates a reversible heating and cooling of the Peltier material, which in direct contact with the elastic waveguide (skull in an example) creates Lamb waves through the thermoelectric mechanism. The structure of the contact region of the thermoelectric material with the skull can be similar to the interdigital one and thus the same considerations apply in order to determine bandwidth and efficiency. Thus we have $k_{in}=2\pi/\Lambda$ for the acoustic input 306, where $\Lambda$ is the period of the stimulus. Here this periodicity is defined by the spacing of the thermal energy peaks, as shown. Thus the pattern of thermal energy provided to the skull of the patient can provide the phase matching to the selected Lamb wave mode.

Absorption of electromagnetic waves in materials such as tissue leads to a fraction of a degree elevation in temperature, which in turn leads to propagation of ultrasound waves through thermoelastic expansion and contraction of tissue (thermoelastic mechanism is when temperature oscillation creates mechanical strain and deformation, also known as thermal strain). Generally when the wavelength is close to the visible region the phenomenon is referred to as optoacoustics or photoacoustics. When it is in the microwave regime, it is called thermoacoustics and in the X-ray regime it is called X-ray acoustics. In all cases, the situation is as shown schematically on FIG. 3D, with a periodic electromagnetic input 312 provided to the skull. The structure of the region over which the substrate (skull surface in one example) is exposed to the electromagnetic wave energy can be similar to the interdigital one and thus the same considerations apply in order to determine bandwidth and efficiency. Thus we have $k_{in}=2\pi/\Lambda$ for the acoustic input 306, where $\Lambda$ is the period of the stimulus. Here this periodicity is defined by the spacing of the electromagnetic energy peaks, as shown. Thus the pattern of electromagnetic radiation provided to the skull of the patient can provide the phase matching to the selected Lamb wave mode.

B) Examples

B1) Wedge Transducer Details

Figure 4:
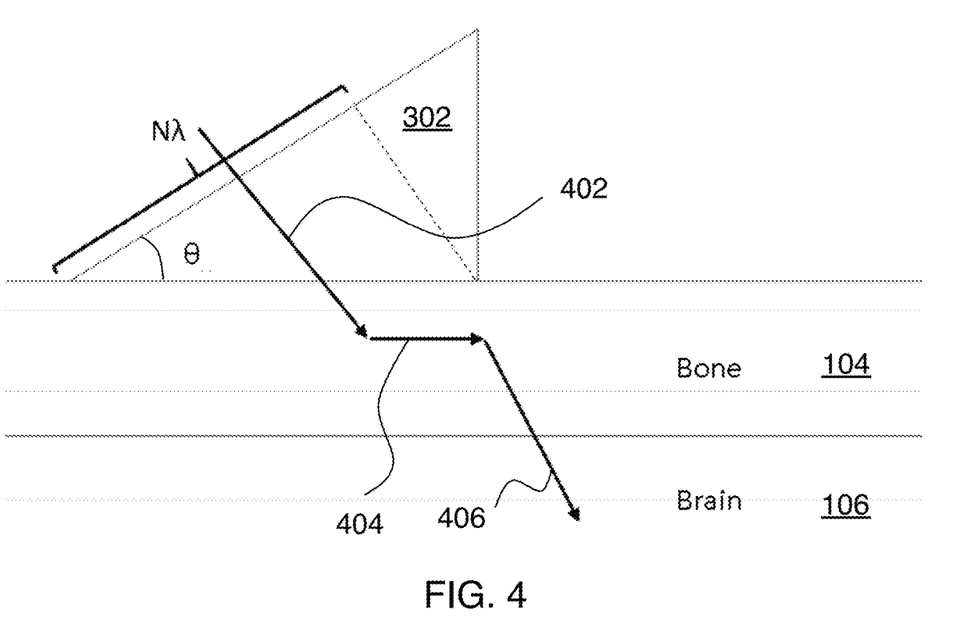
FIG. 4 shows a wedge transducer used to provide an acoustic input that is phase matched to a Lamb mode.

We provide a novel wedge transducer design capable of introducing ultrasound wave energy into the brain through the double-mode-conversion mechanism by selectively exciting leaky guided Lamb waves in the skull. We demonstrate a wedge transducer, by which we can selectively excite one favorable Lamb wave, which in turn propagates a few wavelengths across the skull bone and leaks into the brain. This mechanism is schematically depicted in FIG. 4. The wave 402 generated at the surface of the wedge transducer impinges on the skull at the wedge angle θ. It in turn mode-converts into a suitably selected Lamb mode 404 in the bone, which then propagates a few wavelengths (Nλ) (depending on the wedge length) and leaks into the brain as longitudinal wave 406. The scientific rigor of our approach is due to the proven efficiency and low attenuation of transmitting Lamb waves from a wedge transducer into the brain, through the double-mode-conversion mechanism.

Figure 5A:
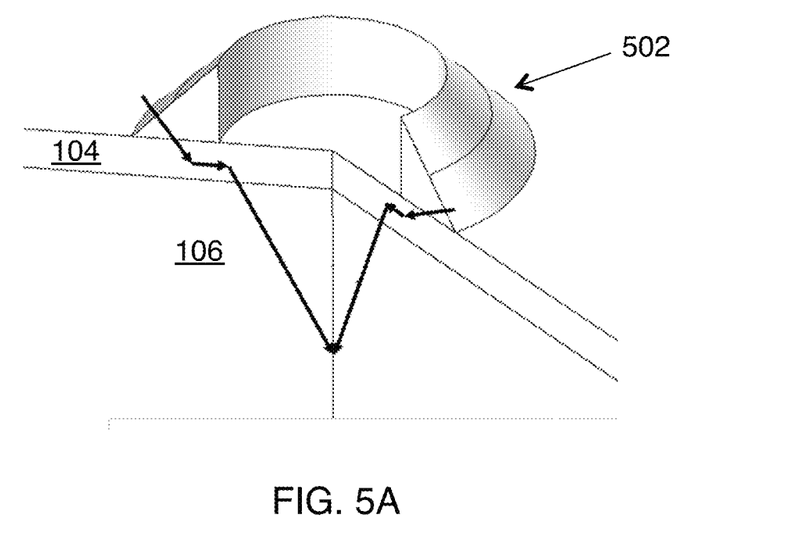
FIGS. 5A-B show exemplary ring-wedge transducer configurations.
Figure 5B:
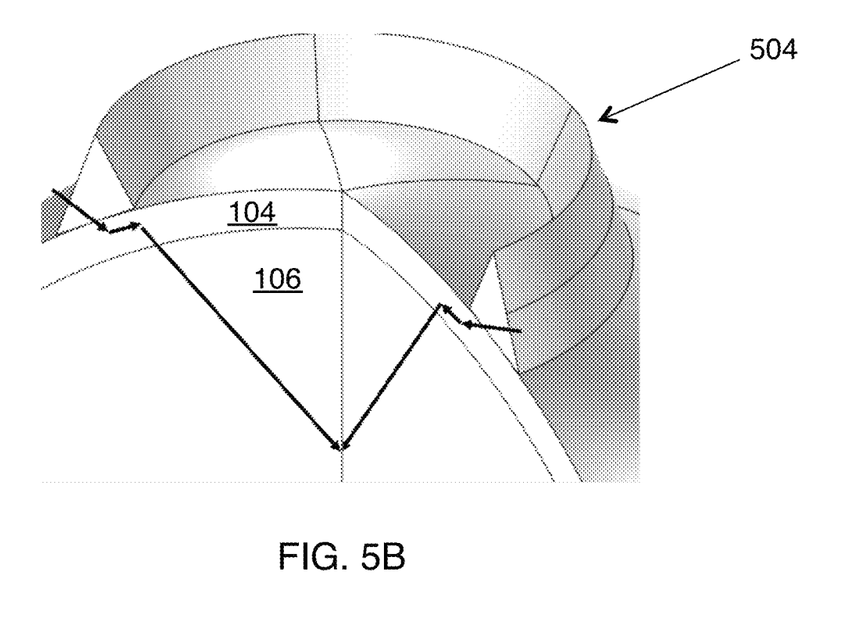

Wedge transducers can be arranged over a ring. This arrangement provides a tight focusing at the focal point that is controlled by the radius of the ring. The ring can be adjusted to have different radii. FIGS. 5A-B show the arrangements of a wedge transducer over a ring, which results in focusing of the leaky Lamb waves inside the brain. The geometry of a human skull is composed of surfaces with different radii of curvature from about 5 cm to about 15 cm. The arrangement of the wedge transducers can be over any contour of any shape, in which case the focusing would be at the center of the area enclosed by the contour. The arrangement can similarly be realized over any three dimensional surface with a particular radius of curvature. For example, FIG. 5A shows a ring-wedge transducer 502 over a flat section of the skull and FIG. 5B shows a ring-wedge transducer 504 over a curved portion of the skull with a finite curvature. Furthermore, the wedge elements can also be phase-shifted. This mechanism, once designed at a specific thickness, is robust to the range of the thicknesses of the skull bone.

Upon selecting the favorable mode dictated by the frequency of interest and its marginal behavior compared to the neighboring modes at that frequency, wedge transducers can be designed to maximize the coupling efficiency of the ultrasound energy into the brain. The critical parameters in a wedge design are the wedge angle and the optimal wedge length, which are functions of the acoustic impedance mismatch between the wedge material and the substrate (the skull bone), and also the frequency. The wedge angle is given by Snell's law; the wedge angle is determined by the ratio of the speed of sound in the wedge to the speed of the guided waves, i.e., $\sin\theta=V_L/V_W$, where $V_L$ is the selected Lamb mode phase velocity (chosen according to the dispersion curve), $V_W$ is the speed of sound of the wedge material, and θ is the wedge angle. As is well known in the art, this velocity matching condition is equivalent to phase matching as described above.

For a wedge transducer, the total loss of transmitting ultrasound energy though skull is the sum of the loss due to attenuation and the loss due to mode-conversion. The loss of Lamb modes is about around 1 dB/mm at 1 MHz for a 5-6 mm thick bone. The propagation path of the desired mode in the skull is about 5-6 mm. This gives around 5-6 dB of loss in the bone. 80% mode-conversion efficiency one way, as argued above, leads to about 4 dB loss due to the double mode-conversion mechanism. Therefore, there exists around 10 dB total transmission loss. On the other hand, for the conventional normal-incident transducer, an average loss of 2 dB/mm at 1 MHz has been reported. This for a 5-6 mm bone results in around 12 dB loss due to attenuation. The direct normal-incident transmission is less than 30%, which gives around 10-11 dB transmission loss. So, in total there is around 22 dB transmission loss for the normal-incident approach. Therefore, the wedge technique outperforms the normal-incident technique by over 10 dB.

Regular geometries such as a sphere may exhibit caustics to acoustic rays. Caustics are regions the rays never visit regardless of the number of reflections inside the geometry. For example, if the ray enters at the angle θ (e.g., the leak angle of the Lamb wave in the skull) into a sphere of radius R, there would be a sphere of radius R cos θ that the ray will never enter. This may inhibit the ability to focus at deep points in the brain. The only case in which the wedge transducers can arbitrarily focus at any point is a flat geometry. However, because of irregularities of real human skulls, this is not expected to be an issue. Moreover, the angle of incidence depends on the selected Lamb mode in the bone, which in turn depends on the wedge material and angle. There is a variety of wedge materials such as PDMS (polydimethylsiloxane) with a low speed of sound (less than 1000 m/s), or Fluorinert™ with an even lower speed of sound (around 500 m/s) that can be utilized to reduce the wedge angle and thereby increase the leak angle, which in turn improves the ability to focus at deep areas of the brain.

B2) Modeling and Experiments

As one specific embodiment, we present a wedge design for the purpose of focusing inside the brain through a skull with an average thickness of 6 mm. This prototype was designed using the third asymmetric Lamb mode of the skull at 1 MHz. Based on the Lamb modes dispersion curves, an asymmetric mode at 1 MHz was chosen, which has the phase velocity of 2105 m/s. In a wedge with a sound speed of 1500 m/s, the wedge angle would be 45° and the optimal wedge length would be N=4λ, where λ=2.105 mm (the Lamb wavelength). The wedge elements are arranged over a ring with a radius of 20 mm.

Figure 6:
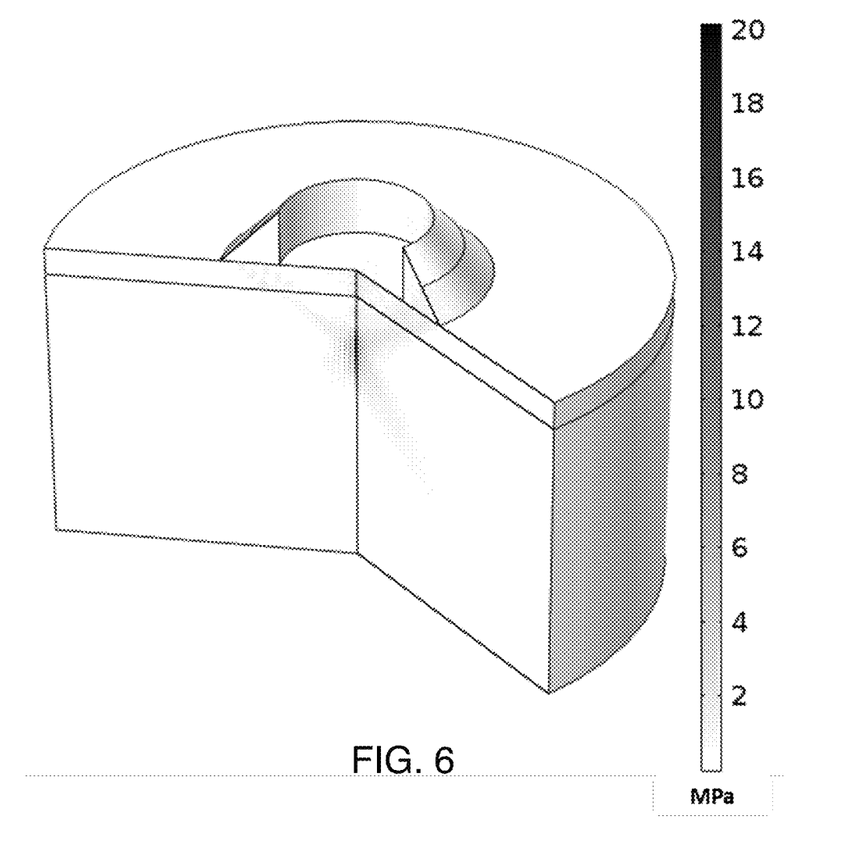
FIG. 6 shows modeled pressure distribution from a ring-wedge transducer.
Figure 7A:
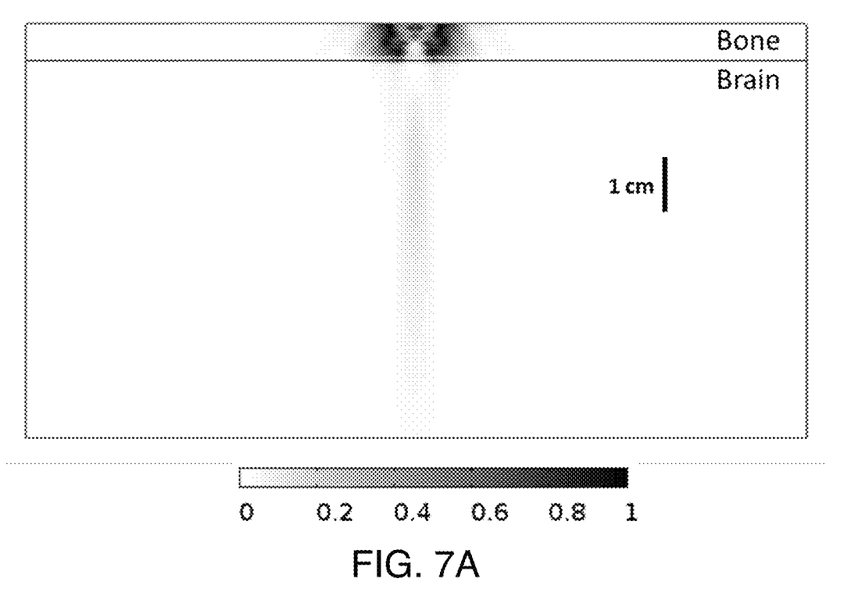
FIG. 7A shows modeled temperature rise from a conventional normal incidence transducer.
Figure 7B:
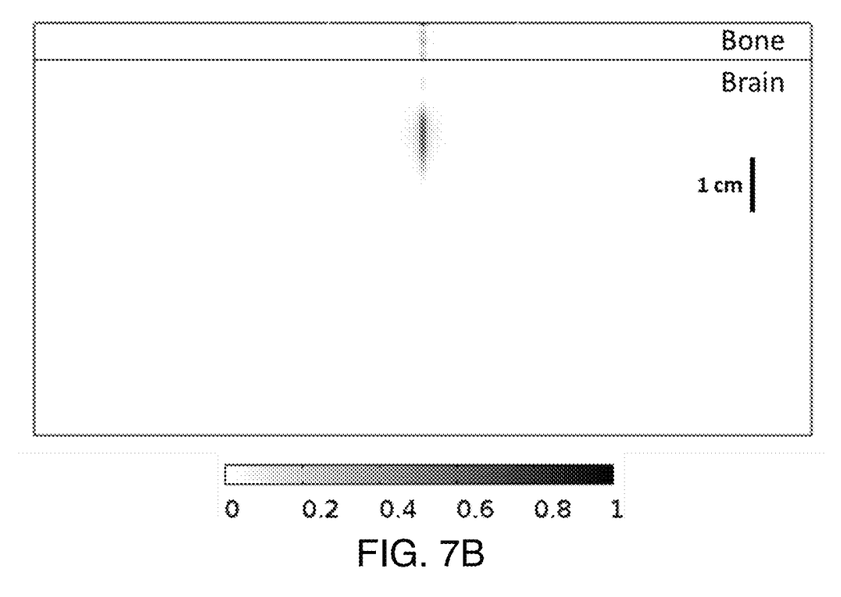
FIG. 7B shows modeled temperature rise from a ring-wedge transducer.

We have conducted several preliminary simulations to verify the concept. A computer simulation showing the performance of a conceptual wedge design is demonstrated in FIG. 6. The wedge elements are arranged over a ring with a radius of 20 mm facing a flat 6-mm thick piece of bone. FIG. 6 shows the focusing of the wedge transducer inside the brain. By adjusting the radius of the wedge ring, different areas of the brain can be targeted. FIGS. 7A-B show a computer simulation that benchmarks a wedge design against a conventional single element normal-beam transducer, both transmitting ultrasound energy through a flat piece of bone. FIGS. 7A (conventional) and 7B (wedge) demonstrate the temperature elevation resulting from both arrays inside the skull relative to the brain, which directly translates into heating in the skull relative to heating inside the brain. Efficient ultrasound power delivery, and thus, minimal temperature rise inside the skull are the main targets of transcranial ultrasound delivery. The plots indicate that in the conventional approach, the temperature rise in the skull greatly exceeds the achievable one in the brain, hence active cooling must be performed to prevent burning of the bone or skin. In contrast, in the present approach, the temperature elevation in the skull is almost negligible compared to the temperature achieved at the focus in the brain.

Figure 8:
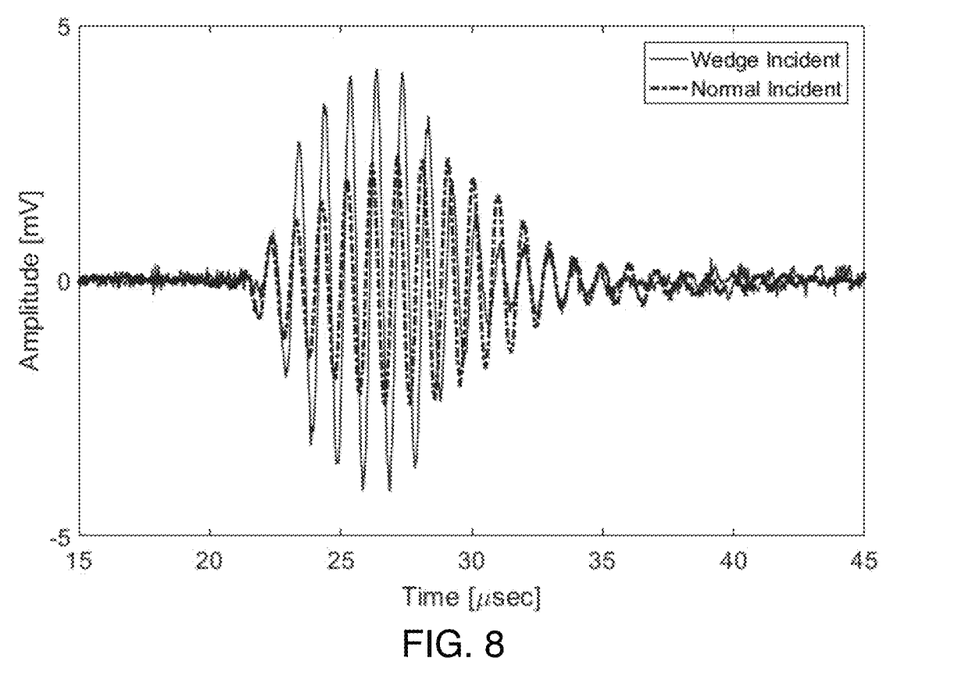
FIG. 8 is a plot of received acoustic amplitude for a normal incidence transducer compared to a wedge transducer.

We utilized a 1 MHz single element commercial transducer (Olympus A303S, 0.5 in diameter) to emulate a wedge transducer. The coupling material between the transducer element and the samples is water, mimicking the effect of the wedge material. Considering water as the wedge material and 2104 m/s the desired Lamb wave phase velocity in the bone leads to a 45° wedge angle. One of the skull fragments, which had been immersed in water for several days, was used along with the single element transducer to benchmark the wedge transmission technique against the normal-incident transmission technique. The skull fragment was placed perpendicular to the ultrasound beam at S1 distance from the surface of the transducer. Here S1 refers to the axial distance from the face of the transducer at which the S parameter of the transducer is equal to 1, where the beam reaches its onset of far-field and its maximum value. $S1=a^2/\lambda$, where a is the radius of the transducer and λ is the wavelength in the medium (in this case water). In the second configuration, the skull fragment was tilted by 38°, to emulate the wedge transmission. The pressure field was measured using a hydrophone. The field measurements are shown in FIG. 8. The wedge technique data shows around 14 dB total loss as opposed to the normal-incident technique, which shows around 21 dB total transmission loss. This is still around 4 dB more loss than expected, which is likely due to the lack of proper alignment of the wedge angle. The true value of the wedge angle must be 45°. However, due to tight spacing between the instruments and the skull fragment, the maximum reachable angle was 38°. This however demonstrates robustness of our approach to angular variability of the wedge.

We have fabricated two wedge transducer prototypes at the Microfab Shop of the Stanford Nano Shared Facilities at Stanford University. 8 mm×6 mm×2 mm PZT-5H piezoelectric plates were bonded to tungsten filled epoxy as the backing layer, in a brass housing. The housing has a 30° angle machined opening on the face. The housing was filled with clear PDMS, providing the wedge material. Clear PDMS has impedance of 1 MRayl, which for the 2104 m/s Lamb phase velocity leads to a 30° wedge angle. The wedge transducers were first characterized to ensure a proper performance. They then were utilized in pitch-catch measurements with and without the skull fragment in between the transmitter and receiver to estimate the total transmission efficiency. The test configurations are schematically shown in FIG. 9A (no skull present between wedges 902 and 904) and FIG. 9B (skull 906 present between wedges 902 and 904).

Figure 9A:
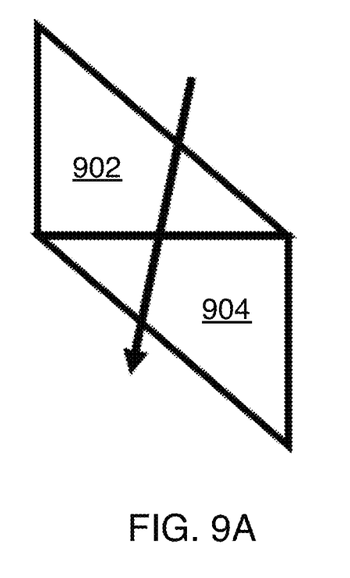
FIG. 9A shows a test configuration for wedge transducers in direct face to face transmission.
Figure 9B:
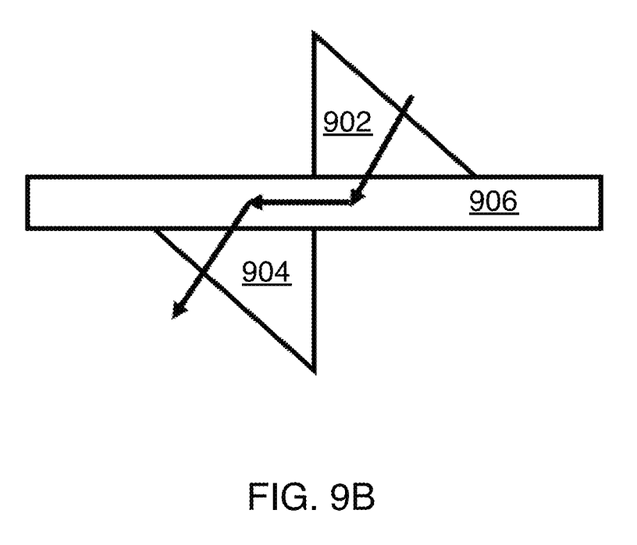
FIG. 9B shows a test configuration for wedge transducers with an intervening layer of skull.
Figure 10A:
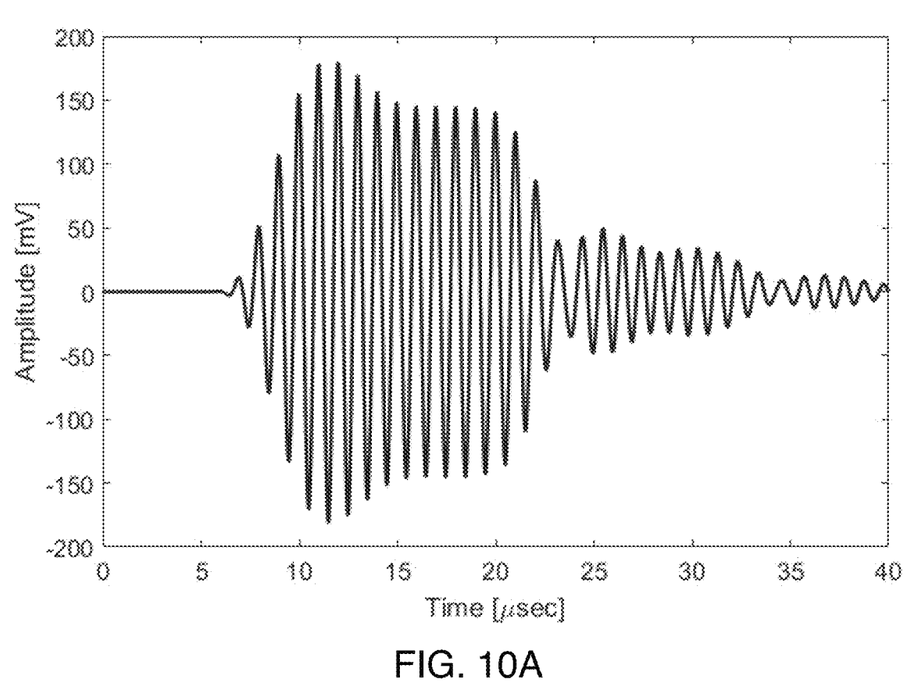
FIG. 10A shows test results for the configuration of FIG. 9A.
Figure 10B:
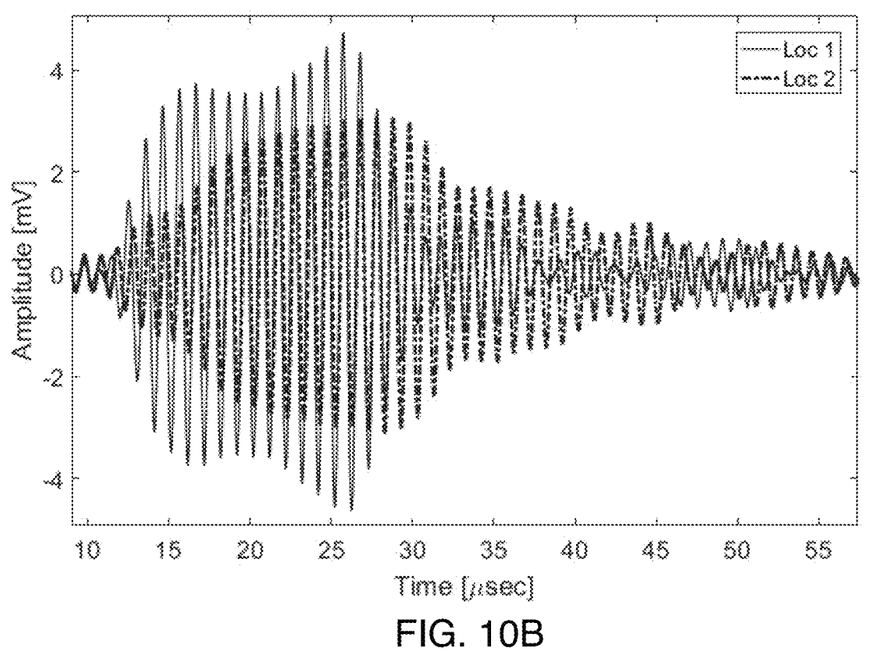
FIG. 10B shows test results for the configuration of FIG. 9B.

The RF data at the receiver are plotted in FIGS. 10A-B, where the results of FIGS. 10A-B correspond to the conditions of FIGS. 9A-B respectively. These results demonstrate that the wedge technique exhibits around 15 dB total loss, around 5 dB more than the expected value, however, still around 7 dB less the normal transmission technique. The excess 5 dB is likely due to lack of proper coupling between the transducer and skull at the inner surface contact, since the skull has a natural curvature and contacting the skull at the inner surface does not provide an optimal coupling with the wedge transducer. Also, since the current prototypes are not water-sealed, the measurements had to be done outside water. Therefore, some of the water filling up the pores of the skull could be draining off, in turning leading to a not-fully-wet skull fragment.

The invention claimed is:

1. Apparatus for providing acoustic energy to a brain of a patient, the apparatus comprising:
   an acoustic transducer configured to excite a selected Lamb wave mode in a skull of the patient via phase matching to the selected Lamb wave mode;
   wherein the selected Lamb wave mode excites a longitudinal acoustic wave in the brain;
   wherein the acoustic transducer comprises a heating element configured to deliver thermal energy to the skull of the patient, and wherein thermal expansion of the skull of the patient excites the selected Lamb wave mode.

2. The apparatus of claim 1, wherein the acoustic transducer is configured as a ring to provide focusing of the longitudinal acoustic wave in the brain.

3. The apparatus of claim 1, wherein the acoustic transducer comprises an electro-mechanical wedge transducer.

4. The apparatus of claim 3, wherein a wedge angle of the electro-mechanical wedge transducer provides the phase matching to the selected Lamb wave mode.

5. The apparatus of claim 1, wherein the acoustic transducer comprises an electro-mechanical interdigitated transducer.

6. The apparatus of claim 5, wherein a periodicity of the electro-mechanical interdigitated transducer provides the phase matching to the selected Lamb wave mode.

7. The apparatus of claim 1, wherein a pattern of thermal energy provided to the skull of the patient provides the phase matching to the selected Lamb wave mode.

* * * * *